(12) United States Patent
Bickford

(10) Patent No.: US 11,660,256 B2
(45) Date of Patent: May 30, 2023

(54) PERFORATED COSMETIC CLOTH

(71) Applicant: L'Oreal, Paris (FR)

(72) Inventor: William Bickford, Scotch Plains, NJ (US)

(73) Assignee: L'Oreal, Paris (FR)

(*) Notice: Subject to any disclaimer, the term of this patent is extended or adjusted under 35 U.S.C. 154(b) by 105 days.

(21) Appl. No.: 16/601,201

(22) Filed: Oct. 14, 2019

(65) Prior Publication Data

US 2021/0106504 A1 Apr. 15, 2021

(51) Int. Cl.
*A61K 8/02* (2006.01)
*A47K 7/00* (2006.01)
*A45D 34/00* (2006.01)

(52) U.S. Cl.
CPC .............. *A61K 8/0208* (2013.01); *A47K 7/00* (2013.01)

(58) Field of Classification Search
CPC ........ A61K 8/0208; A47K 7/00; A45D 34/00; A45D 2200/1036; A45D 2200/1027
See application file for complete search history.

(56) References Cited

U.S. PATENT DOCUMENTS

| 6,206,902 B1 * | 3/2001 | Morikane ............... A61Q 19/00 602/41 |
| 6,638,527 B2 | 10/2003 | Gott et al. |
| 7,122,238 B2 | 10/2006 | Macedo |
| 8,689,387 B2 | 4/2014 | Gundersen |
| 2012/0230750 A1 | 9/2012 | Golden |

FOREIGN PATENT DOCUMENTS

| FR | 2946236 A1 | 4/2012 |
| GB | 2489737 A | 10/2012 |
| JP | H11318559 A | 11/1999 |
| WO | 2013/72157 A1 | 5/2013 |
| WO | 2018234286 A1 | 12/2018 |

OTHER PUBLICATIONS

International Search Report and Written Opinion dated Mar. 3, 2021, issued in corresponding International Application No. PCT/US2020/055512, filed Oct. 14, 2020, 12 pages.

* cited by examiner

*Primary Examiner* — Trevor Love
(74) *Attorney, Agent, or Firm* — Christensen O'Connor Johnson Kindness PLLC

(57) ABSTRACT

A cosmetic wipe for applying or removing a cosmetic formula is described. In an embodiment, the cosmetic wipe includes a thin body. The cosmetic wipe also includes an edge of the body defining a perimeter of the body and a slit located in the thin body offset from the edge of the body. The slit may be configured to increase an edge length of the body.

5 Claims, 2 Drawing Sheets

PERFORATED COSMETIC CLOTH

SUMMARY

The present disclosure is directed to, among other things, representative embodiments of a cosmetic wipe for applying or removing a cosmetic formula. In an embodiment, the cosmetic wipe includes a thin body. The cosmetic wipe also includes an edge of the body defining a perimeter of the body and a slit located in the thin body offset from the edge of the body. The slit may be configured to increase an edge length of the body.

Various embodiments of the present disclosure may include different configurations of the slit. For example, in an embodiment, the slit may be perforated. In an embodiment, the slit may include at least one rounded slit inward or offset from the edge of the body. In an embodiment, the slit may include a series of symmetric rounded slit offset from the edge of the body.

Various embodiments of the present disclosure may include different configurations or characteristics of the body. Of course, embodiments of present disclosure may include two or more of the following in any combination. For example, the cosmetic wipe in an embodiment may include a first face of the body and a second face of the body opposite the first face. In an embodiment, the first face has a first surface texture and the second face has a second surface texture. In an embodiment, a thickness of the body may be between 2 millimeters and 8 millimeters. In an embodiment, a pile of the material may be between a negligible measurement and 10 millimeters. In an embodiment, the thin body may comprise one of a fabric, open-cell foam, and non-woven material. The body in an embodiment may be one of dissolvable material and a reusable material.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
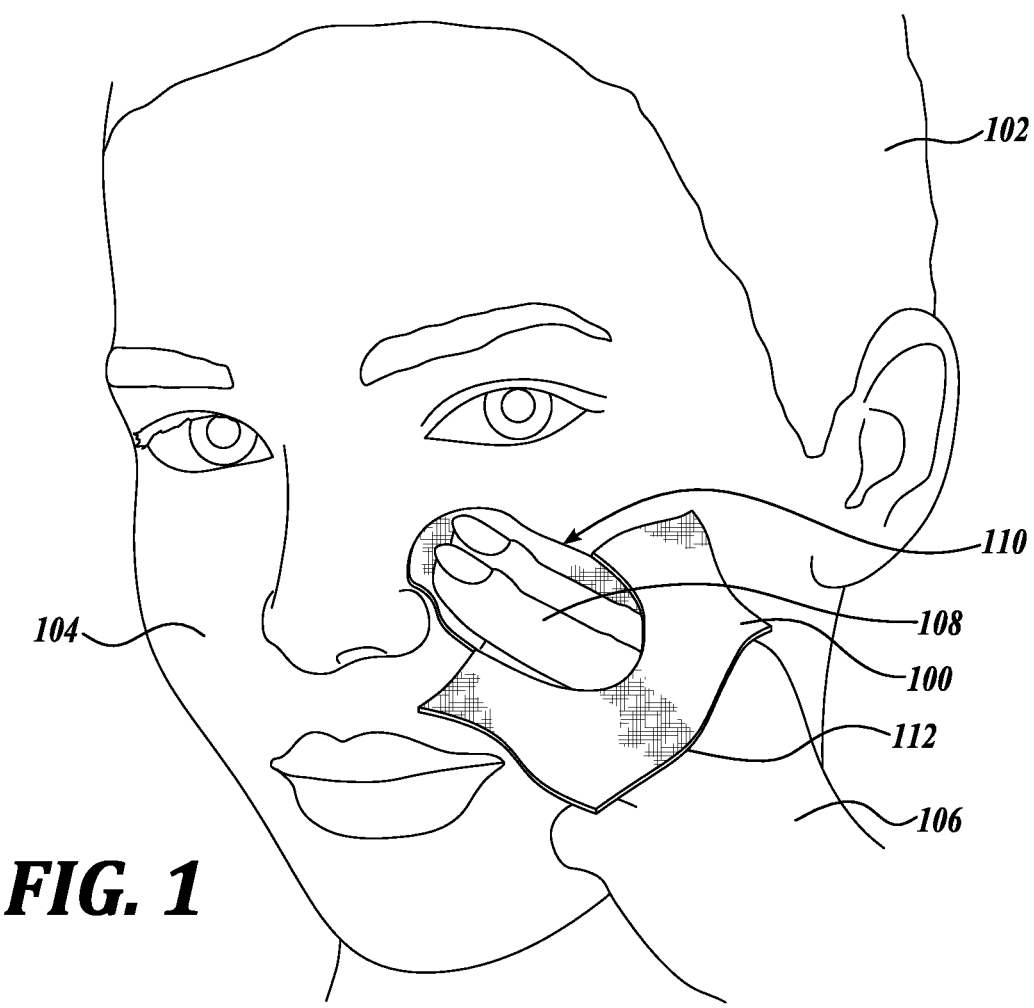
FIG. 1 is a schematic of a person using a representative embodiment of a cosmetic wipe in accordance with an aspect of the present disclosure.
Figure 2:
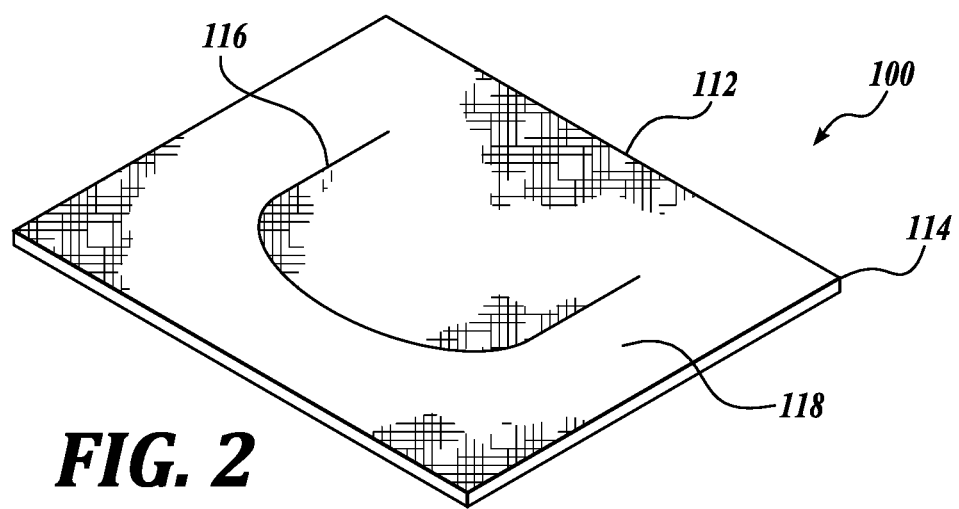
FIG. 2 is a perspective view of the cosmetic wipe of FIG. 1.

The following description provides several examples that relate to cosmetic wipes. Application or removal of a wide variety of cosmetic formulas to the human body is a common practice, including face, eyelashes, eyelids, eyebrows, fingernails, toenails, lips, and other body parts. Some examples of such cosmetic formula include primer, mascara, eyeliner, eye shadow, concealer, foundation, powder, blush, bronzer, highlighter, nail polish, lipstick, lip gloss, etc. To apply or remove the cosmetic formula, a cosmetic wipe can be used. The wipe may be specific to a particular application or use, or may be generally used for multiple functions. Generally described, a cosmetic wipe includes a thin material such as a nonwoven or fabric material. In some embodiments, the cosmetic wipe may be scented, perfumed, or otherwise enhanced with various additives.

When using the cosmetic wipe, users may often utilize an edge of the body of the wipe to either apply or remove a cosmetic formula as described herein. The edge of the body of the wipe may be a thin edge and enable the user to use the wipe with an increased amount of precision. Additionally, most cosmetic wipes may be square or rectangular in shape. Some applications or uses of the wipes may be improved with rounded edges or other non-linear edge patterns. For example, a rounded edge surface may be more beneficial for specific applications such as nailbeds, eye regions, nose regions, and the like. A curved edge may more readily adapt to specific body parts than a linear edge.

In some embodiments, a wipe of the present disclosure may incorporate an increased edge length without changing an overall shape or size of the wipe. For example, to increase overall wipe use efficiency and, in some embodiments, to reduce overall consumer waste, a cosmetic wipe may incorporate an increase in edge length or edge portions. In some embodiments of the present disclosure, the wipe design may increase the edge portions of the wipe without changing an overall outer shape of the cosmetic wipe. For example, in some embodiments, the cosmetic wipe may incorporate one or more slits into the body of the wipe. The slits may be formed by either one or more continuous through-slits or by one or more perforated portions.

In some embodiments, the type of slit may be specific to the type of material used to manufacture the wipe and the targeted use of the wipe. For example, a through-slit may be cut clean into the cosmetic wipe such that the wipe inherently has a lengthened edge length. In other embodiments, a perforated slit may enable the user to sever the perforations and increase the edge length as desired or needed. The type of slit may also depend upon other wipe characteristics. Of course, embodiments of the wipes may include both a through-slit and a perforated slit. For example, a wipe with both a through-slit and a perforated slit may be employed for multiple different uses or applications.

In some embodiments, the cosmetic wipe may be impregnated with a cosmetic formula to apply to a part of the body. For example, the wipe may be impregnated with sunscreen, blush, bronze, concealer, or the like and may enable a user to apply the cosmetic formula to the desired part of their body. Having a precise edge may enable the user to apply the formula with precision and ease. In alternative embodiments, the wipe may be impregnated a different type of formula to remove a cosmetic formula or cleanse a body part. For example, the wipe may be impregnated with make-up remover, cleanser, nail polish remover, or the like. The wipe may enable a user to remove make-up, nail polish, or other cosmetics. It may also enable a user to remove dirt, toxins, and other pollutants from their skin. In some embodiments, the wipe may be used to blot away oils or other materials from the user's skin. A wipe with an increased edge length may enable users to more effectively and efficiently use the wipe for the targeted use.

In some examples herein, we may use removal of a cosmetic formula for clarity and brevity. However, it is understood that any wipe disclosed herein may also be additionally or alternatively used to apply a cosmetic formula. Accordingly, the detailed description is not meant to narrow the use or embodiments of the wipe but is for exemplary purposes only.

FIG. 1 depicts a use of a representative embodiment of a cosmetic wipe 100 in accordance with the present disclosure. Generally, a user 102 may be using the cosmetic wipe 100 to, for example, remove a cosmetic formula from their face 104. The user 102 may use their hands 106 and pick-up the cosmetic wipe 100 and, with their fingers 108, may separate a slit-edge 110. In the embodiment shown, the slit-edge 110 is rounded. The rounded slit-edge 110 may enable a user to precisely remove makeup from targeted locations, such as the nose area as shown. For example, using any edge 112 of the cosmetic wipe 100 may enable precision makeup removal. However, an overall contour of an edge may also increase the precision removal of makeup in specific situations.

Referring generally to FIGS. 2 and 3A-3D, the cosmetic wipe 100 will be described in more detail. The cosmetic wipe 100 may come in any standard shape, typically a square or a rectangle. The square or rectangular shape may reduce waste during production. Other shapes may also reduce waste such as a triangle or hexagon. Each of these shapes produces little to no waste in a base product of the cosmetic wipe 100. The polygonal shapes of the cosmetic wipe 100 may result in a very edge section 112 with corners 114 where the linear edges 112 meet.

The cosmetic wipe 100 includes a body 118 having an edge 112 defining a perimeter thereof. The body 118 is provided with an inset slit 116 that is positioned inwardly of the edge 112 of the body 118. In the embodiments shown, the slit 116 is drawn as a through-slit. However, it should be understood that the slit may also be a perforated slit. In some embodiments, the slit 116 may be a through-slit which forms a complete incision through the body 118 of the cosmetic wipe 100. In this instance, the cosmetic wipe 100 may have a first outer edge 112 and a second, inner slit-edge 110. The incision may immediately increase the length of edge contained with the body 118 of the cosmetic wipe 100.

In alternative embodiments, the slit 116 may be a series of incisions through the body 118 of the cosmetic wipe 100 such that the slit 116 is a series of perforations that may need to be broken to create the slit-edge 110. A perforated slit may provide the user with the option of perforating the slit 116 to increase the amount of edge provided within a given cosmetic wipe 100. The perforated slit may enable the user to completely separate the slit 116, to optionally only perforate a section the user deems necessary for the given application, or to not perforate the slit 116 and retain the cosmetic wipe 100 in its entirety. In some embodiments, each slit may be formed solely with through-slit sections, solely with perforated slit-sections, or with both through-slit and perforated sections.

Figure 3A:
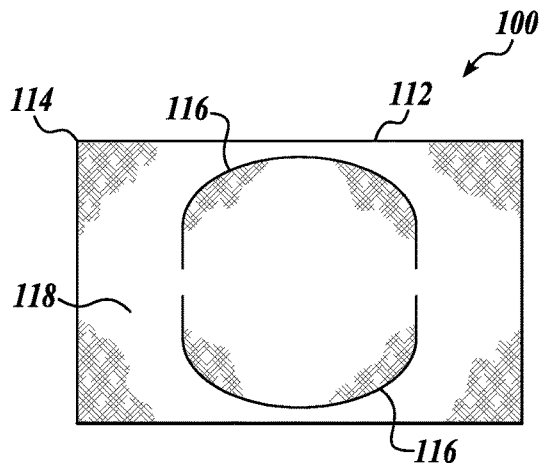
FIGS. 3A-D are plan views of various embodiments of a cosmetic wipe with difference slit configurations.
Figure 3B:
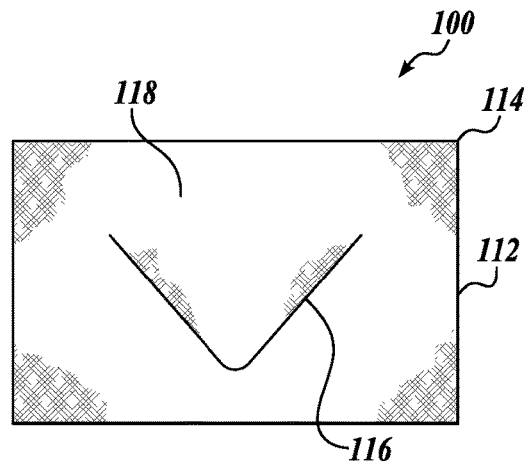
Figure 3C:
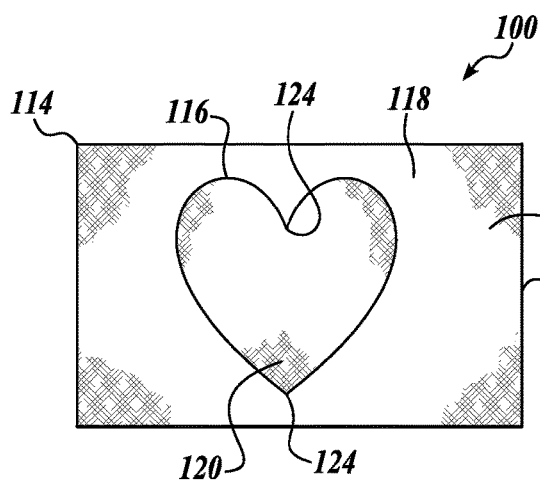
Figure 3D:
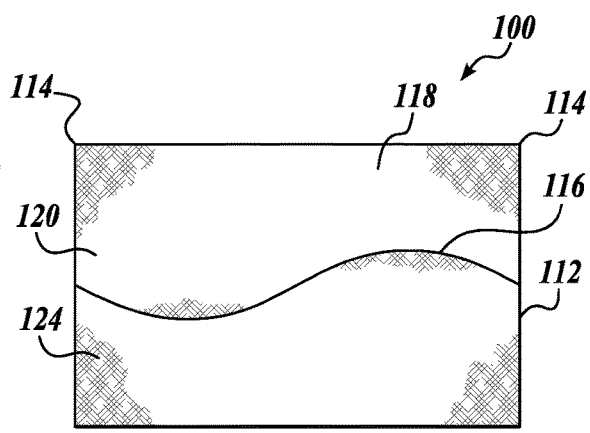

The slit 116 may have a variety of configurations as shown in FIGS. 3A-3D, and more not pictured. For example, the slit 116 may be rounded as shown in FIG. 3A, linear as shown in FIG. 3B, fanciful, or mimic a shape as shown in FIG. 3C. In some embodiments, as shown in both FIGS. 3C and 3D, the slit 116 may separate the cosmetic wipe 100 into a first portion 120 of the body 118 and a second portion 122 of the body 118. As shown in FIGS. 3B-3C, the slit 116 may have pointed or rounded corners 124, or may not have any corners as shown in FIGS. 3A and 3D.

As further shown in FIGS. 3C and 3D, the slit 116 may be S-shaped, star shaped, heart-shaped, or any other shape which may be appealing to a user. In some embodiments, as shown in FIG. 3A, the cosmetic wipe 100 may also have more than one slit 116, each slit 116 either mirroring the other as shown, or each slit 116 forming its own unique configurations. In some of these embodiments, both slits 116 may be through-slits, perforated slits, or one through-slit and one perforated slit Additionally, each slit may be formed with through-slit sections, perforated slit-sections, or both. The configurations may be tailored to a specific use or may be generic to offer a user a more varied utilization of the cosmetic wipe 100.

In some embodiments, as shown in exemplary embodiments in FIGS. 3C and 3D, if the slit is a perforated slit 116, the perforated slit 116 may be positioned such that, if perforated, the cosmetic wipe 100 may be split into a first portion 120 of the cosmetic wipe 100 and a second, separate portion 122 of the cosmetic wipe 100. In some embodiments, the perforated slit 116 may be positioned approximately down a middle of the cosmetic wipe 100. In further embodiments, the perforated slit 116 may be offset from a centerline of the cosmetic wipe 100. The cosmetic wipe 100 may also include multiple perforated slits 116 which may separate the cosmetic wipe 100 into multiple sections.

The perforated slit 116 may enable a user to utilize the edge 112 of the cosmetic wipe 100 and then perforate the cosmetic wipe 100 into two portion 120, 122 and increase a length of the edge 112 by generating the slit-edge portion 110. In an alternative embodiment, the user may also perforate the slit 116 and then place the second piece 122 back into a package of wipes 100 to use later. This may enable the user to reduce their waste and only utilize a portion of the cosmetic wipe 100 needed for immediate use.

In some embodiments, the slit 116 may be linear or may be curved or follow another shaped line. For example, a non-linear configuration of the slit 116 may provide the user with a curved shape. The curved shape of the slit 166 may still enable a user to have a varied option of edge shapes for various uses. In some embodiments, the cosmetic wipe 100 may have a single, splitting slit 116, which may essentially divide the cosmetic wipe 100 into two separate portions.

In further embodiments, the cosmetic wipe 100 may have multiple splitting slits 116 which may divvy the cosmetic wipe 100 into other configurations such as thirds, quarters, multiple shapes, or the like. In still further embodiments, the perforated split 116 may not half the cosmetic wipe 100 but may separate the cosmetic wipe 100 into multiple pieces wherein the cosmetic wipe 100 may have a rectangular outer-shape with a void the middle body 118. For example, as shown in FIG. 3C, the splitting slit 116 may separate the cosmetic wipe 100 into two different components where a first component 120 is a shape and the second component 122 retains the outer edge 112 shape with a hole in a center of the body 118. In further embodiments, the first component 120 may be of any polygonal shape or any other shape.

Figure 4:
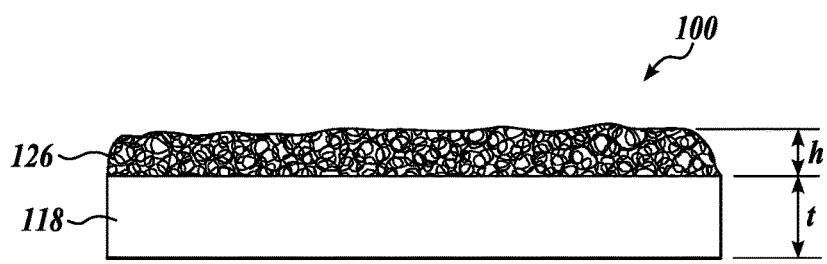
FIG. 4 is a side view of various embodiments of the cosmetic wipes of FIGS. 2 and 3A-3D.

The cosmetic wipe 100 may be manufactured with a variety of materials in various configurations. In some embodiments, the material may include nonwoven or fabric materials including cellulose, viscose, polypropylene fibers, bamboo fibers, cactus fibers, polyethylene fibers, and the like. As shown in FIG. 4, a thickness t of the cosmetic wipe 100 may vary from thin to thick, for example between ½ mm to 8 mm, or between 2 mm and 4 mm. Additionally, as shown in FIG. 4, a pile 126 of the cosmetic wipe 100 may vary depending upon the base material and the intended end use of the wipe. For example, in some embodiments, the pile 126 of the cosmetic wipe 100 may be negligible to non-existent. This may provide a smooth surface of the cosmetic wipe 100. In other embodiments, a height h of the pile 126 may vary between 1 mm to 10 mm. The height h of the pile 126 may depend on the type of material and targeted use of the cosmetic wipe 100. For example, the cosmetic wipe 100 may have a high pile 126 which may provide more absorption. A rougher surface may also provide more exfoliation abilities.

In some embodiments, the cosmetic wipe 100 may be a single material or may be either a hybrid material or several materials combined to form the body 118 of the cosmetic wipe 100. A hybrid material cosmetic wipe 100 may have a surface of the cosmetic wipe 100 that is relatively smooth compared to a second surface of the cosmetic wipe 100. The difference in smoothness or roughness may enable the user to determine which face of the cosmetic wipe 100 to use for the specific application. For a multi-material cosmetic wipe 100, each face of the cosmetic wipe 100 may comprise a different material to provide the user with a varied experience. In a multi-material configuration, one of the materials may comprise a waterproof material. In another embodiment, the cosmetic wipe 100 may comprise multiple layers of the same or different material.

In further embodiments, the cosmetic wipe 100 may be dry or may be saturated with a variety of cosmetic formulas. If the cosmetic wipe 100 is dry, the cosmetic wipe 100 may be hydroponic and the cosmetic wipe 100 may retain the desired cosmetic formulas applied to the cosmetic wipe 100. In other embodiments, the cosmetic wipe 100 may act as a transfer agent to apply a cosmetic formula such as a make-up (i.e., foundation, concealer, blush, bronzer, etc.). In further embodiments, the cosmetic wipe 100 may be saturated with a cosmetic formula such as make-up, make-up remover, nail polish remover, acetone, or the like.

In some embodiments, the cosmetic wipe 100 may be disposable, compostable, or reusable. For example, the cosmetic wipe 100 may comprise a compostable material such as cellulose, bamboo, or another material. The material may break down over time which may enable the user to reduce their footprint. In alternative embodiments, the cosmetic wipe 100 may be reusable. For example, the cosmetic wipe 100 may be hand-washable or machine-washable and enable the user to reuse the cosmetic wipe 100.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "front," "back," "upward," "downward," "right hand," "left hand," "lateral," "medial," "in," "out," "extended," "advanced," "retracted," "proximal," "distal," "central," etc. These references, and other similar references in the present application, are only to assist in helping describe and understand the particular embodiment and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A cosmetic wipe for applying a cosmetic formula, the wipe comprising:
   a thin body having an edge defining a perimeter of the body;
   a through-slit which forms a complete incision through the thin body of the cosmetic wipe; and
   the through-slit is located within the perimeter of the body, and increases an edge length of the body, wherein the through-slit starts and ends within the perimeter of the body, wherein the through-slit includes opposite first and second straight edge portions connected by a curved or angled edge portion, the through-slit is unconnected from the body except by an area opposite from the curved or angled edge portion and between the start and end of the through-slit,
   wherein the cosmetic wipe is a single material to form the thin body, wherein the material is selected from one of a fabric, an open-cell foam, and a non-woven;
   wherein the cosmetic wipe is impregnated with at least one from sunscreen, blush, bronze, and concealer.

2. The cosmetic wipe of claim 1, wherein a thickness of the body is between about 2 millimeters and about 8 millimeters.

3. The cosmetic wipe of claim 1, wherein the body is one of dissolvable material and a reusable material.

4. The cosmetic wipe of claim 1, comprising multiple layers of the same material.

5. A cosmetic wipe for applying a cosmetic formula, the wipe comprising: a thin body having an edge defining a perimeter of the body;
   a through-slit which forms a complete incision through the thin body of the cosmetic wipe; and the through-slit is located within the perimeter of the body, and increases an edge length of the body, wherein the through-slit starts and ends within the perimeter of the body, wherein the through-slit includes opposite first and second straight edge portions connected by a curved or angled edge portion, the through-slit is unconnected from the body except by an area opposite from the curved or angled edge portion and between the start and end of the through-slit, wherein the cosmetic wipe includes several materials to form the thin body, wherein the several materials are selected from a fabric, an open-cell foam, and a non-woven;

wherein the cosmetic wipe is impregnated with at least one from sunscreen, blush, bronze, and concealer.

\* \* \* \* \*